United States Patent
Romano et al.

(10) Patent No.: US 11,471,068 B2
(45) Date of Patent: Oct. 18, 2022

(54) DETERMINING AN AIRWAY FLOW LIMITATION VALUE

(71) Applicant: KONINKLIJKE PHILIPS N.V., Eindhoven (NL)

(72) Inventors: Robert Romano, Pittsburgh, PA (US); Mark Christopher McDermott, Pittsburgh, PA (US); Peter Douglas Hill, Murrysville, PA (US); Richard Anthony Bates, Allison Park, PA (US)

(73) Assignee: Koninklijke Philips N.V., Eindhoven (NL)

( * ) Notice: Subject to any disclaimer, the term of this patent is extended or adjusted under 35 U.S.C. 154(b) by 332 days.

(21) Appl. No.: 16/098,598

(22) PCT Filed: May 9, 2017

(86) PCT No.: PCT/EP2017/060978
§ 371 (c)(1),
(2) Date: Nov. 2, 2018

(87) PCT Pub. No.: WO2017/194495
PCT Pub. Date: Nov. 16, 2017

(65) Prior Publication Data
US 2019/0142301 A1 May 16, 2019

Related U.S. Application Data

(60) Provisional application No. 62/334,066, filed on May 10, 2016.

(51) Int. Cl.
*A61B 5/087* (2006.01)
*A61B 5/00* (2006.01)
(Continued)

(52) U.S. Cl.
CPC ............ *A61B 5/087* (2013.01); *A61B 5/4836* (2013.01); *A61B 5/7225* (2013.01);
(Continued)

(58) Field of Classification Search
CPC ..... A61B 5/087; A61B 5/4836; A61B 5/7225; A61B 5/7246; A61B 5/746;
(Continued)

(56) References Cited

U.S. PATENT DOCUMENTS

| 4,289,142 A | * | 9/1981 | Kearns | ............... A61B 5/02455 600/536 |
| 6,814,074 B1 | | 11/2004 | Nadjafizadeh | |

(Continued)

FOREIGN PATENT DOCUMENTS

WO WO2015184187 A2 12/2015

OTHER PUBLICATIONS

Bitmasks—For Beginners. Codeforces, Bitmasks—For Beginners, Nov. 19, 2015 (Year: 2015).*

(Continued)

*Primary Examiner* — Devin B Henson
*Assistant Examiner* — Justin Xu
(74) *Attorney, Agent, or Firm* — Daniel H. Brean

(57) ABSTRACT

A system for determining an airway flow value in a patient is provided. The system comprises a computer system that comprises one or more physical processors programmed with computer program instructions which, when executed cause the computer system to obtain, from one or more health monitoring devices, airway pressure information of the patient and airway flow information of the patient; determine an airway flow limitation index from the airway pressure information of the patient and the airway flow information of the patient; and determine the airway flow limitation value for the patient by comparing the determined
(Continued)

airway flow limitation index with an airway flow limitation threshold value. The airway flow limitation value indicates a number of breaths of the patient that are flow limited in a given time period.

11 Claims, 7 Drawing Sheets

(51) Int. Cl.
*A61M 16/00* (2006.01)
*A61M 16/10* (2006.01)
(52) U.S. Cl.
CPC ............ *A61B 5/7246* (2013.01); *A61B 5/746* (2013.01); *A61M 16/024* (2017.08); *A61M 16/10* (2013.01); *A61M 2016/003* (2013.01); *A61M 2016/0027* (2013.01); *A61M 2205/3553* (2013.01); *A61M 2205/3592* (2013.01); *A61M 2205/502* (2013.01); *A61M 2205/52* (2013.01)
(58) Field of Classification Search
CPC ........ A61M 2205/52; A61M 2016/003; A61M 2205/3553; A61M 2016/0027; A61M 16/10; A61M 2205/502; A61M 2205/3592; A61M 16/024
See application file for complete search history.

(56) References Cited

U.S. PATENT DOCUMENTS

| 7,270,128 | B2 | 9/2007 | Berthon-Jones | |
|---|---|---|---|---|
| 10,194,834 | B2 | 2/2019 | Narasimhan | |
| 2004/0187869 | A1* | 9/2004 | Bjorndal | G09B 23/288 |
| | | | | 128/200.23 |
| 2005/0143617 | A1* | 6/2005 | Auphan | A61M 21/00 |
| | | | | 600/26 |
| 2006/0070625 | A1* | 4/2006 | Ayappa | A61M 16/0051 |
| | | | | 128/204.23 |
| 2008/0097234 | A1 | 4/2008 | Nicolazzi | |
| 2010/0108066 | A1* | 5/2010 | Martin | A61M 16/0069 |
| | | | | 128/204.23 |
| 2010/0147305 | A1 | 6/2010 | Aliverti et al. | |
| 2010/0328075 | A1* | 12/2010 | Rahamim | A61B 5/6808 |
| | | | | 340/573.1 |
| 2011/0196251 | A1* | 8/2011 | Jourdain | A61M 16/026 |
| | | | | 600/538 |
| 2012/0010519 | A1 | 1/2012 | Ayappa et al. | |
| 2012/0105193 | A1 | 5/2012 | Gritti | |
| 2013/0289364 | A1* | 10/2013 | Colman | A61M 16/0069 |
| | | | | 600/301 |
| 2014/0200474 | A1* | 7/2014 | Selvaraj | A61B 5/0806 |
| | | | | 600/529 |
| 2015/0320955 | A1* | 11/2015 | Mahadevan, Jr. | |
| | | | | A61M 16/0003 |
| | | | | 128/204.23 |
| 2016/0361012 | A1 | 12/2016 | Chen et al. | |

OTHER PUBLICATIONS

Manipulating Non-Byte-Sized Data in Java. Department of Computer Science: University of Waikato (Year: 2013).*
Rees, K. et al. "Frequency and Significance of increased upper airway resistance during sleep", American Journal of Respiratory and Critical Care Medicine., vol. 162, No. 4, (Oct. 1, 2000), pp. 1210-1214.
Clark S A et al., "Assessment of Inspiratory Flow Limitation Invasively and Non-invasively during Sleep", American Journal of Respiratory and Critical Care Medic, American Lung Association, New York, NY, US, vol. 1, 58, Jan. 1, 1998 (Jan. 1, 1998), pp. 713-722, XP008121364.

* cited by examiner

DETERMINING AN AIRWAY FLOW LIMITATION VALUE

CROSS-REFERENCE TO RELATED APPLICATIONS

This patent application claims the priority benefit under 35 U.S.C. § 371 of international patent application no. PCT/IB2016/052252, filed Apr. 21, 2016, which claims the priority benefit under 35 U.S.C. § 119(e) of U.S. Provisional Application No. 62/334,066, filed on May 10, 2016, the contents of which are herein incorporated by reference.

BACKGROUND OF THE INVENTION

1. Field of the Invention

The present disclosure pertains to a method and an apparatus for facilitating treatment of a patient and, more particularly, determining an airway flow limitation value for a patient and/or controlling, based thereon, a health device facilitating treatment of the patient.

2. Description of the Related Art

Airway flow limitation is a physiological condition where a person's airways partially collapse due to a loss of their elastic recoil due to parenchymal destruction or to some other form of airway obstruction.

Currently, clinicians have limited ability to quantifiably assess whether a particular airway pressure therapy is effective in the treatment of a patient's airway flow limitation that isn't either invasive or difficult to set-up on the patient. Subsequently, there are no current indices to guide the clinician for the appropriate and/or optimal airway pressure therapy and prescription to treat a patient's airway flow limitation. Therefore, an improved system for informing a clinician, in real time, of a patient's pulmonary status is desired.

SUMMARY OF THE INVENTION

Accordingly, it is an object of one or more embodiments of the present patent application to provide a system for determining an airway flow limitation value in a patient. The system comprises a computer system that comprises one or more physical processors programmed with computer program instructions which, when executed cause the computer system to: obtain, from one or more health monitoring devices, airway pressure information of the patient and airway flow information of the patient; determine an airway flow limitation index from the airway pressure information of the patient and the airway flow information of the patient; and determine the airway flow limitation value for the patient by comparing the determined airway flow limitation index with an airway flow limitation threshold value. The airway flow limitation value indicates a number of breaths of the patient that are flow limited in a given time period.

It is yet another aspect of one or more embodiments of the present patent application to provide a method for determining an airway flow limitation value in a patient. The method is implemented by a computer system that comprises one or more physical processors executing computer program instructions which, when executed, perform the method. The method comprises obtaining, from one or more health monitoring devices, airway pressure information of the patient and airway flow information of the patient; determining, by the computer system, an airway flow limitation index from the airway pressure information of the patient and the airway flow information of the patient; and determining, by the computer system, the airway flow limitation value for the patient by comparing the determined airway flow limitation index with an airway flow limitation threshold value. The airway flow limitation value indicates a number of breaths of the patient that are flow limited in a given time period.

It is yet another aspect of one or more embodiments to provide a system for determining an airway flow limitation value in a patient. The system comprises a means for executing machine-readable instructions with at least one processor. The machine-readable instructions comprises obtaining, from one or more health monitoring devices, airway pressure information of the patient and airway flow information of the patient; determining an airway flow limitation index from the airway pressure information of the patient and the airway flow information of the patient; and determining the airway flow limitation value for the patient by comparing the determined airway flow limitation index with an airway flow limitation threshold value. The airway flow limitation value indicates a number of breaths of the patient that are flow limited in a given time period.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
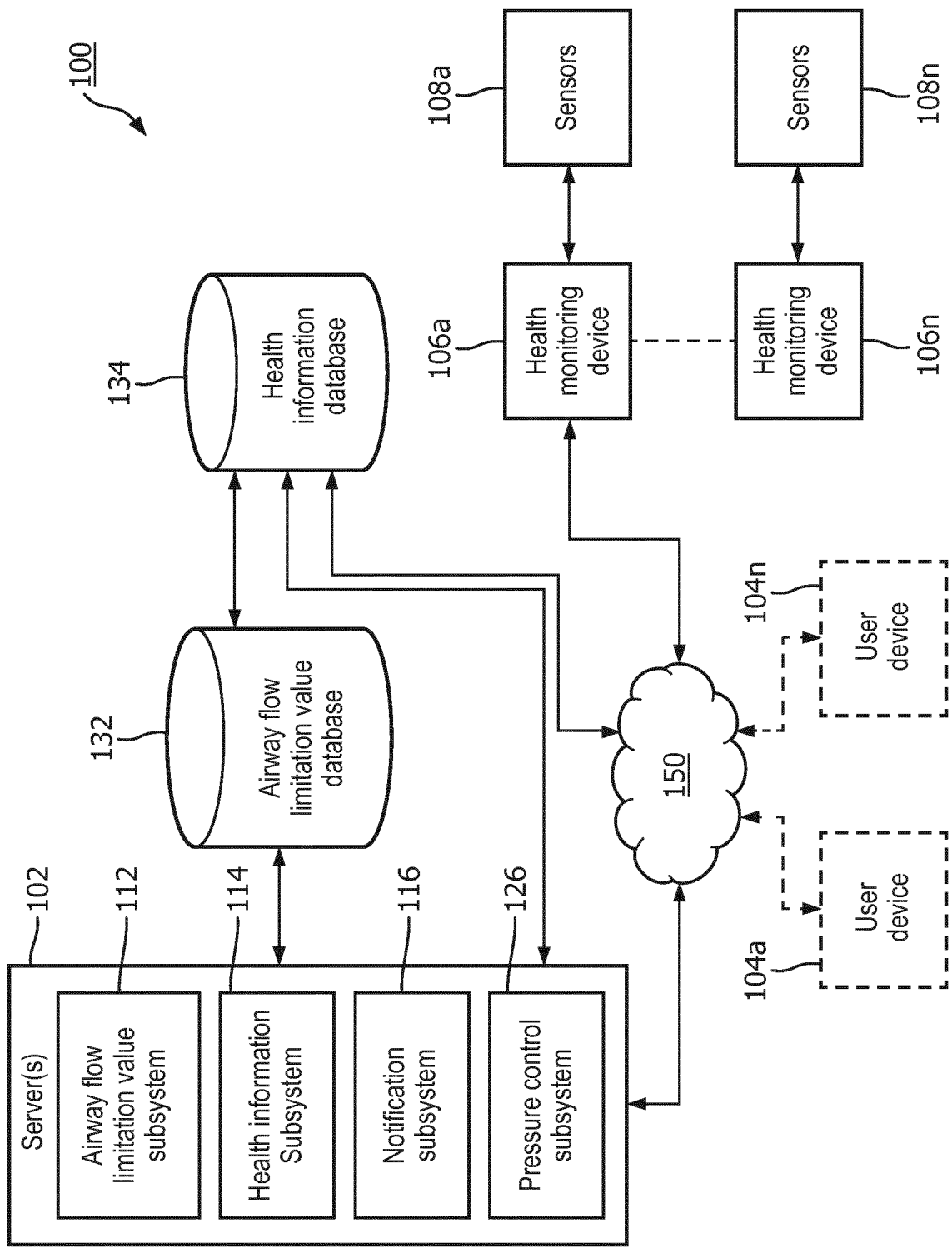
FIG. 1 is an exemplary system for determining an airflow limitation value in a patient in accordance an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present patent application provides a system 100 for determining an airway flow limitation value in a patient. As will be clear from the discussions below, in one embodiment, ssystem 100 includes a computer system 102 that has one or more physical processors programmed with computer program instructions which, when executed cause computer system 102 to obtain, from one or more health monitoring devices 106 (e.g., 106a . . . 106n), airway pressure information of the patient and airway flow information of the patient; determine an airway flow limitation index from the airway pressure information of the patient and the airway flow information of the patient; and determine the airway flow limitation value for the patient by comparing the determined airway flow limitation index with an airway flow limitation threshold value. The airway flow limitation value indicates a number of breaths of the patient that are flow limited in a given time period.

In one embodiment, system 100 is configured for describing the effectiveness of a pressure therapy/treatment given to a patient by determining and displaying the airway flow limitation value. In some embodiments, the airway flow limitation value is a number or a percentage of a patient's breaths that have airway flow limitation. For example, the higher the number or percentage of airflow limited breaths, the greater the ineffectiveness of the pressure therapy/treatment. If the percent of flow limited breaths is at or near 0%, the pressure therapy/treatment is optimally effective. Whereas, if the percentage of flow limited breaths is closer to 100%, the pressure therapy/treatment is ineffective or minimally effective. It has been demonstrated and widely accepted that the number of breaths that have flow limitation (e.g., expiratory) can be reduced by the application of positive pressure (e.g., during the expiratory phase) of a person's breath cycle. System 100 is also configured for controlling or adjusting (e.g., pressure) the effectiveness of a pressure therapy/treatment given to a patient based on the determined airway flow limitation value. In one embodiment, the positive expiratory pressure (PEP) can then be increased until the percentage of flow limited breaths is at its nadir.

FIG. 1 shows system 100 for determining an airway flow limitation value in a patient, in accordance with one or more embodiments. As shown in FIG. 1, system 100 may comprise server 102 (or multiple servers 102). Server 102 may comprise airway flow limitation value subsystem 112, health information subsystem 114, notification subsystem 116, pressure control subsystem 126 or other components or subsystems.

In one embodiment, the patient is on a telemedicine, telehealth or telecare service. In one embodiment, the telehealth service is configured to facilitate a medical encounter or an interaction between the patient at a patient site and a provider at a provider site remotely located from the patient.

System 100 may include user device 104 (or multiple user devices 104a-104n). User device 104 may comprise any type of mobile terminal, fixed terminal, or other device. By way of example, user device 104 may comprise a desktop computer, a notebook computer, a tablet computer, a smartphone, a wearable device, or other user device. Patients may, for instance, utilize one or more user devices 104 to interact with server 102 or other components of system 100. It should be noted that, while one or more operations are described herein as being performed by components of server 102, those operations may, in some embodiments, be performed by components of user device 104 or other components of system 100. In some embodiments, user device(s) 104 are optional.

In some embodiments, health information subsystem 114 may obtain health information associated with a patient. Upon obtainment, the health information may be stored (e.g., health information database 134, or other storage if not already stored therein). In some embodiments, the health information may include airway flow information, airway pressure information, airway volume information, or any other airway related information.

As another example, the health information may be obtained from one or more health monitoring devices (e.g., airway flow monitoring device, airway pressure monitoring device, airway volume monitoring device or other health monitoring devices). These health monitoring devices may include one or more sensors, such as pressure sensors, pressure transducers, flow rate sensors, volume sensors, or other sensors. The sensors may, for instance, be configured to obtain health information of the patient (e.g., airway pressure, airway flow, airway volume, or any other airway parameters) or other health information related to the patient.

In one scenario, a health monitoring device may obtain health information (e.g., based on information from one or more sensors), and provide health information to a computer system (e.g., comprising server 102) over a network (e.g., network 150) for processing. In another scenario, upon obtaining the health information, the health monitoring device may process the obtained health information, and provide processed health information to the computer system over a network (e.g., network 150). In yet another scenario, the health monitoring device may automatically provide health information (e.g., obtained or processed) to the computer system (e.g., comprising server 102). If, for instance, the health monitoring device is offline (e.g., not connected to the Internet, not connected to the computer system, etc.), the health monitoring device may store the health information and provide the health information to the computer system when the health monitoring device comes online (e.g., when the online status is detected by an application of the user device).

In some embodiments, health information subsystem 114 may continuously obtain subsequent health information associated with the multiple patients. As an example, the subsequent health information may comprise additional health information corresponding to a subsequent time (after a time corresponding to health information that was used to determine the airway flow limitation value for the patient). As an example, the subsequent health information may be obtained from one or more health monitoring devices. The subsequent health information may be utilized to further update or modify the airway flow limitation threshold value (e.g., new health information may be used to dynamically update or modify the airway flow limitation threshold value), etc.

In some embodiments, airway flow limitation subsystem 112 determines an airway flow limitation value for the patient. In some embodiments, the airway flow limitation value indicates a number or a percentage of breaths of the patient that are flow limited in a given time period.

In some embodiments, the airway flow limitation value is an expiratory airway flow limitation value. As an example, system 100 is configured to provide the number or percentage of a patient's breaths that is indicative of limited airway flow breaths during expiration. In some embodiments, the airway flow limitation value is an inspiratory airway flow limitation value. As an example, system 100 is configured to provide the number or percentage of a patient's breaths that is indicative of limited airway flow breaths during inspiration.

In some embodiments, system 100 is configured to determine whether a normal breathing/respiration pattern is detected and whether a stable mask interface is detected. In some embodiments, airway flow limitation subsystem 112 determines the airway flow limitation value for the patient, when a normal breathing/respiration pattern of a patient is detected and a stable mask interface on the patient is detected. In some embodiments, system 100 may include sensors for sensing the breathing/respiration pattern of a patient. System 100 may also be configured to compare the breathing/respiration pattern signals from the sensors to a predetermined breathing/respiration pattern to determine whether the sensed breathing/respiration pattern is normal. In some embodiments, system 100 may include sensors for sensing whether a stable mask interface is provided for a patient.

In some embodiments, airway flow limitation subsystem 112 is configured to obtain, from one or more health monitoring devices 106a . . . 106n, airway pressure information of the patient, airway flow information of the patient, respiratory or airway volume information of the patient, or other information related to the patient. In some embodiments, the airway flow information of the patient may include information about flow at the airway opening of the patient (e.g., information specifying resistance to airflow at the airway opening during inspiration or expiration, information specifying flow rate at the airway opening during inspiration or expiration, or other information). In some embodiments, the airway pressure information of the patient may include information about pressure at the airway opening of the patient (e.g., information specifying airway pressure at the airway opening during inspiration or expiration or other information). In some embodiments, the airway pressure information of the patient may include information about esophageal pressure (e.g., information specifying airway pressure in the esophagus during inspiration or expiration or other information).

In some embodiments, one or more health monitoring devices 106a . . . 106n may comprise airway pressure monitoring device, airway volume monitoring device, airway flow monitoring device, or other airway monitoring devices. In some embodiments, one or more health monitoring devices 106a . . . 106n may be configured to monitor respiratory or airway volume. In some embodiments, one or more health monitoring devices 106 may be configured to monitor flow at the airway opening. In some embodiments, one or more health monitoring devices 106a . . . 106n may be configured to monitor pressure at the airway opening. In some embodiments, one or more health monitoring devices 106a . . . 106n may be configured to monitor esophageal pressure.

In some embodiments, airway flow limitation subsystem 112 is configured to determine an airway flow limitation index from the obtained airway pressure information of the patient, the obtained airway flow information of the patient, or other airway or airway flow related information. That is, airway flow limitation subsystem 112 is configured to analyze information/data from a device's flow and pressure sensors and calculate an airflow limitation index based on the sensor data/information. For example, the airflow limitation index is a measurement that represents the degree of a patient's pulmonary airways' flow limitation. The airflow limitation index may then be used to determine the airway flow limitation value for the patient. As explained in detail below, the determined airflow limitation value for the patient is displayed as a single term generically labelled and referenced as "Percent Flow Limited Breaths". In some embodiments, this term, or terms similar, may be used to describe either the number or percentage of 'expiratory flow limited breaths' or 'inspiratory flow limited breaths.'

In some embodiments, the airway flow limitation index, AFLI or $\Delta Xrs$ may be determined as the mean difference between mean value of respiratory system reactance during inspiration, Mean-$Xrs_{insp}$ and mean value of respiratory system reactance during expiration, Mean-$Xrs_{exp}$ as shown in Equation (1) below. In some embodiments, the airway flow limitation index, $\Delta Xrs$ that is calculated using the Equation (1) below has high sensitivity and high specificity around a threshold value.

$$\Delta Xrs = \text{Mean-}Xrs_{insp} - \text{Mean-}Xrs_{exp} \quad (1)$$

In some embodiments, respiratory system impedance is a ratio of the Fourier transforms of the obtained airway pressure information and obtained airway flow information. In some embodiments, the real and imaginary parts of the respiratory system impedance are the resistance of the respiratory system and reactance of the respiratory system. In some embodiments, respiratory system reactance may be determined using the obtained airway pressure information and obtained airway flow information.

In some embodiments, the airway flow limitation index may be determined using mean value of respiratory system reactance during expiration, Mean-$Xrs_{exp}$. In some embodiments, the airway flow limitation index may be determined using minimum value of respiratory system reactance during expiration, Min-$Xrs_{exp}$.

In some embodiments, the airway flow limitation index, AFLI may be determined as the difference between maximum value of respiratory system reactance during inspiration, Max-$Xrs_{insp}$ and minimum value of respiratory system reactance during expiration, Min-$Xrs_{exp}$ as shown in Equation (2) below.

$$AFLI = \text{Max-}Xrs_{insp} - \text{Min-}Xrs_{exp} \quad (2)$$

In some embodiments, airway flow limitation value subsystem 112 is configured to determine the airway flow limitation value for the patient by comparing the determined airway flow limitation index with the airway flow limitation threshold value.

In some embodiments, the airway flow limitation threshold value may be a value above which a breath is to be considered "flow limited." In some embodiments, the airway flow limitation threshold value may be 2.7 cm $H_2O$/sec/L. In some embodiments, the airway flow limitation threshold value may be obtained by clinical testing. In some embodiments, the airway flow limitation threshold value may be obtained using data analytics. In some embodiments, the airway flow limitation threshold value may be obtained from research publications.

Figure 5:
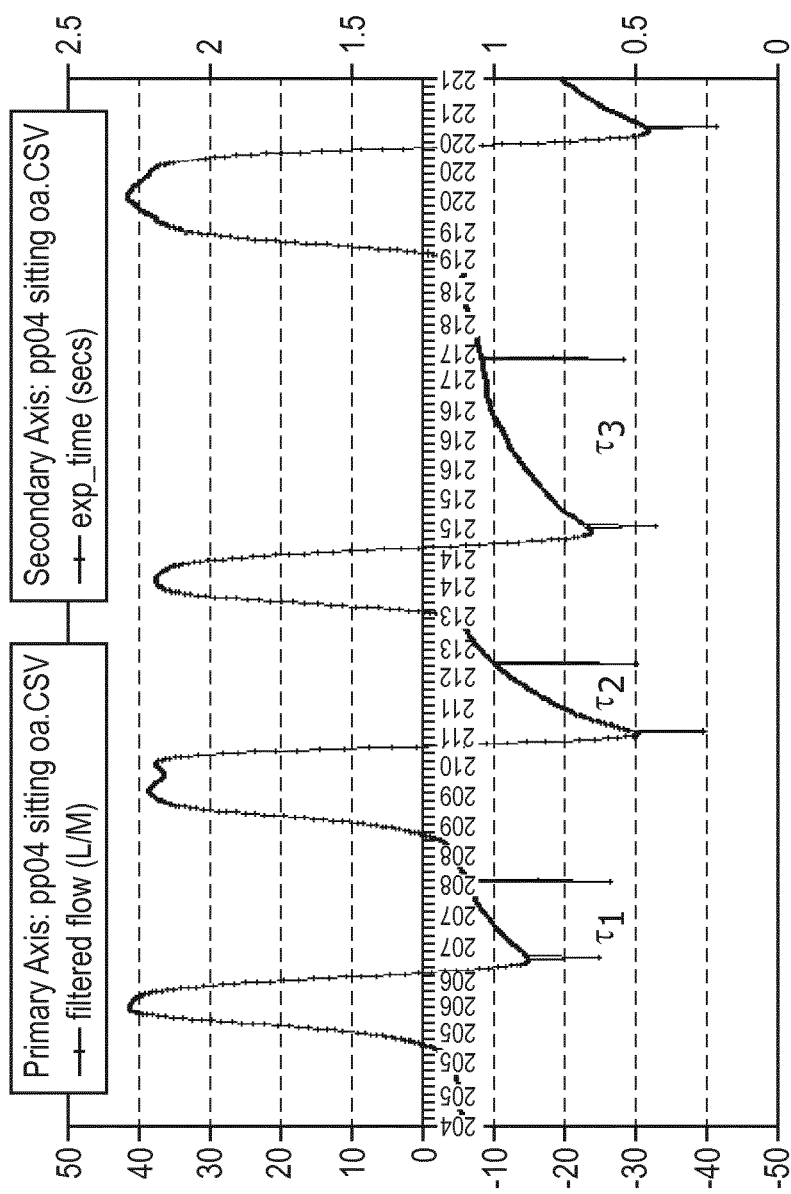
FIG. 5 is an exemplary representation of an index that may be used in determining an airway flow limitation threshold value in accordance an embodiment of the present patent application.

In some embodiments, referring to FIG. 5, an index is used to determine the airway flow limitation threshold value. For example, as shown in FIG. 5, a time constant between two time periods that could occur anywhere along a direct or derived signal (in this case, airway flow in (Liters/min, L/min or L/m)) during a phase of a breathing cycle (in this case, expiration). The time constants $\tau_1$, $\tau_2$ and $\tau_3$ (as shown in FIG. 5) can be processed to determine the airway flow limitation threshold value.

In some embodiments, the airway flow limitation threshold value is set a certain percentage above the threshold value used by system 102, with the intention of filtering out normal variances that would oscillate around a single threshold value.

In some embodiments, airway flow limitation value subsystem 112 is configured to determine the airway flow limitation threshold value using previously obtained airway pressure information from a plurality of patients and previously obtained airway flow information from the plurality of patients. In some embodiments, airway flow limitation value subsystem 112 is also configured to continuously obtain subsequent airway pressure information of the plurality of patients and subsequent airway flow information of the plurality of patients. In some embodiments, airway flow limitation value subsystem 112 is configured to then continuously modify or update the airway flow limitation threshold value based on the subsequent airway pressure information, the subsequent airway flow information, or other subsequent information.

In some embodiments, the determined airway flow limitation threshold value may be saved into a database (e.g., airway flow limitation value database 132) and retrieved from the database as needed. As described above, airway flow limitation value subsystem 112 may continuously update/modify different airway flow limitation threshold values. For example, in some embodiments, patients having severe symptoms may have a different airway flow limitation threshold value than the patients having mild symptoms.

Figure 2:
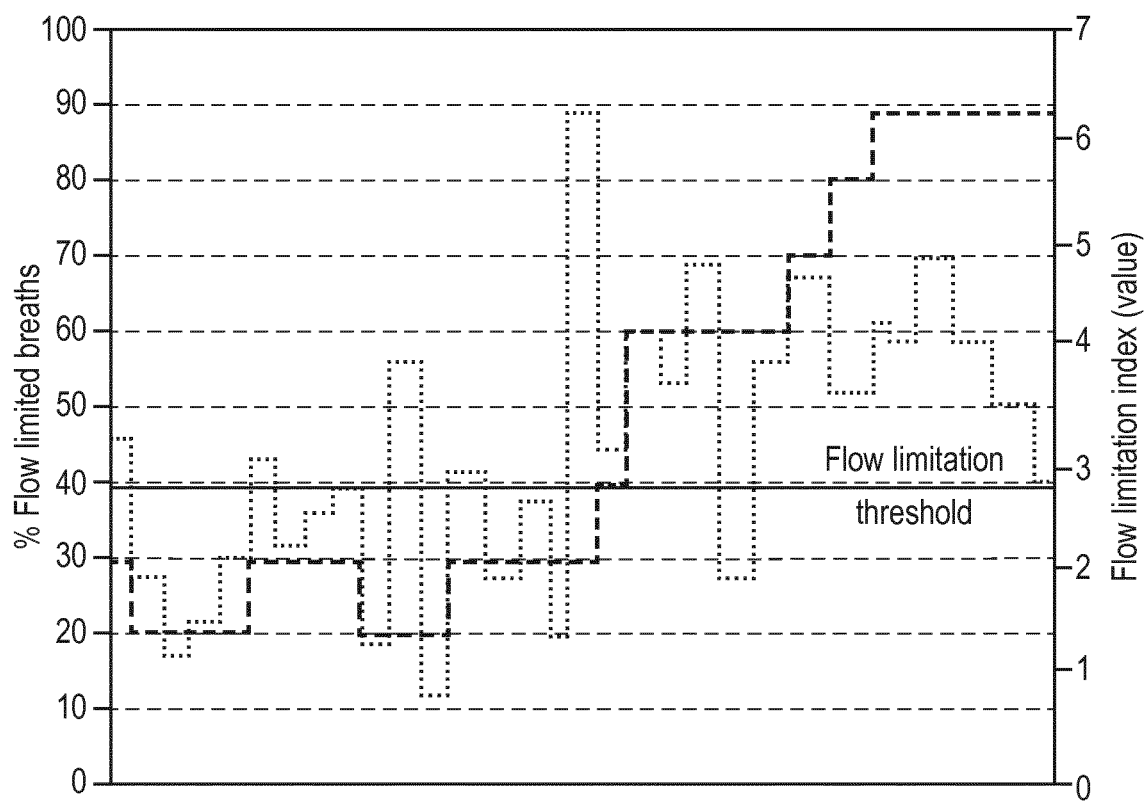
FIG. 2 is a graphical illustration of airway flow limitation index, airway flow limitation threshold value and the airway flow limitation value for the patient in accordance an embodiment of the present patent application.

FIG. 2 shows a graphical illustration of a response of the airway flow limitation value (i.e., percent flow limited breaths) to the airway flow limitation index when the airway flow limitation index is either above or below the airway flow limitation threshold value. The graph in FIG. 2 illustrates the airway flow limitation value (i.e., percent flow limited breaths) and the airway flow limitation index on its vertical Y-axis and the breath count on its horizontal X-axis. (The airway flow limitation value for the patient is determined based on a percentage or a number of valid breaths within a given number of total breaths (or a period of time) that are above airway flow limitation threshold value.

Figure 7A:
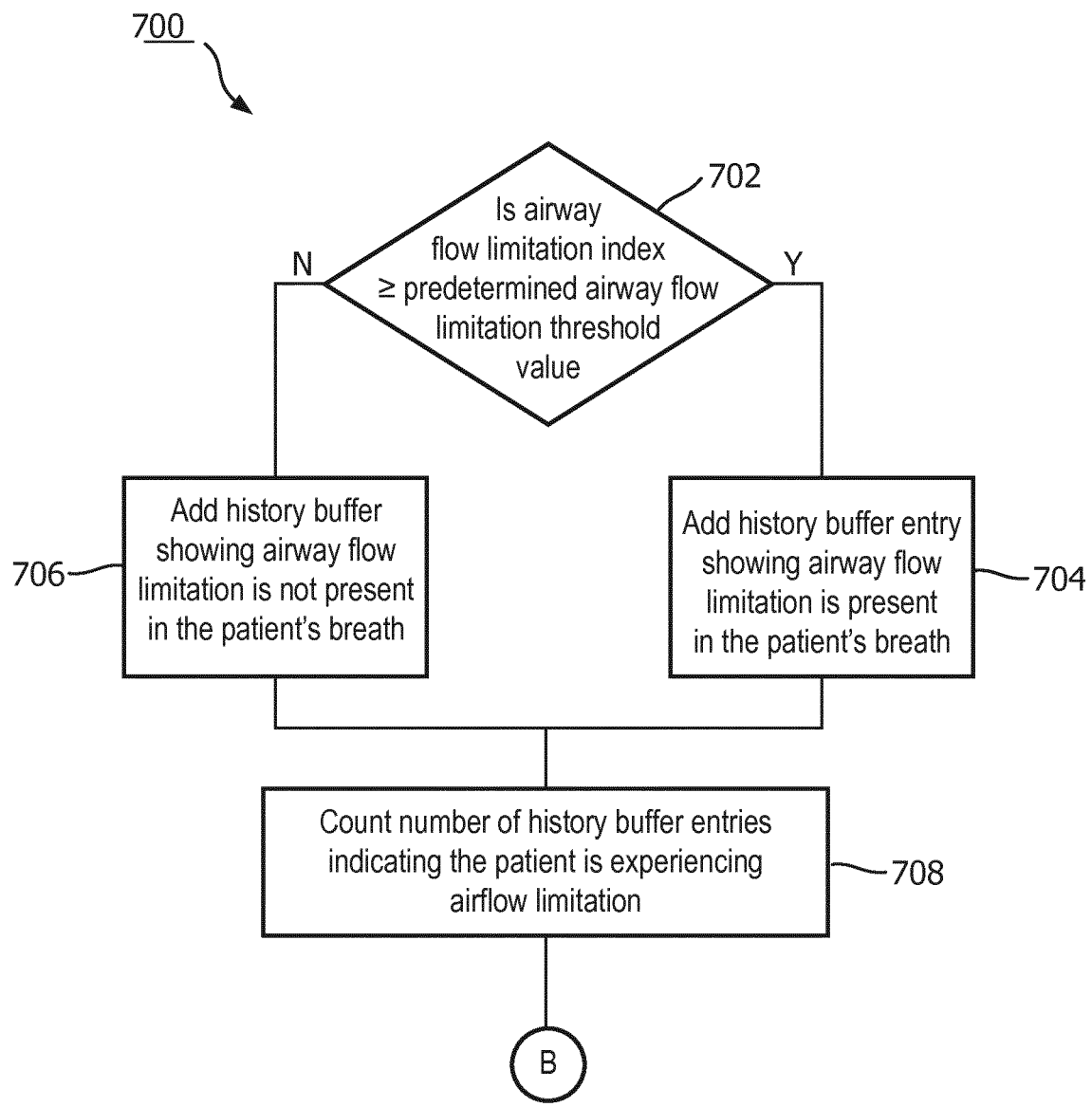
FIGS. 7A and 7B show another flow chart for determining an airflow limitation value in a patient in accordance an embodiment of the present patent application.
Figure 7B:
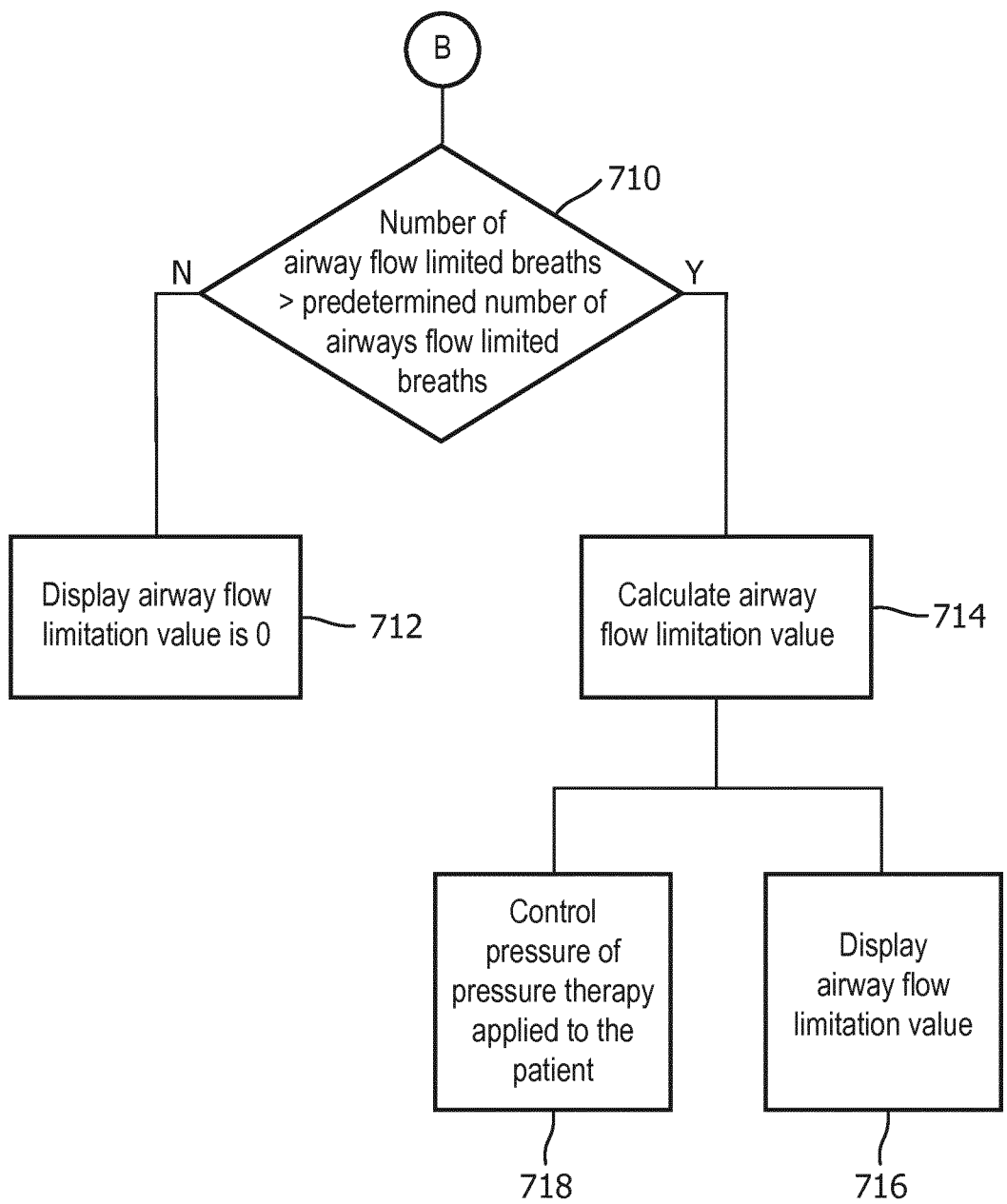

FIGS. 7A and 7B show a method 700 (and flow chart) for determining the airflow limitation value in the patient in accordance an embodiment of the present patent application. In some embodiments, a comparison between the determined airway flow limitation index and the airway flow limitation threshold value is performed at procedure 702 of method 700 in FIGS. 7A and 7B.

In some embodiments, system 102 is configured to maintain a history of the flow limited breaths. For example, the flow limited breaths history is maintained as a 32-bit bitmask, where each bit represents a sample breath in the history. In some embodiments, each bit may be turned "OFF" (bit is "0") when the sample/breath is determined not to have an airway flow limitation and turned "ON" (bit is "1") when the sample/breath is determined to have an airway flow limitation. In some embodiments, the number of bits in the bitmask may vary.

In some embodiments, each time a sample/breath is added to the history, the bitmask is shifted one place to the right. In some embodiments, airway flow limitation value subsystem 112 is configured to use an airway flow limited breath history wrap mask to limit the history to a predetermined number of samples/breaths. For example, the airway flow limited breath history wrap mask is used to limit the history to 20 samples/breaths. In some embodiments, the number of samples/breaths in the history buffer may vary.

Referring to FIGS. 7A and 7B, if the determined airway flow limitation index is greater than or equal to the airway flow limitation threshold value, airway flow limitation value subsystem 112 is configured to add history buffer entry showing airway flow limitation is present in the patient's breath (e.g., at procedure 704 of method 700). In some embodiments, airway flow limitation value subsystem 112 is configured to turn a bit "ON" (bit is "1"), when it is determined that the airway flow limitation index is greater than or equal to the airway flow limitation threshold value.

If the determined airway flow limitation index is less than the airway flow limitation threshold value, airway flow limitation value subsystem 112 is configured to add history buffer entry showing airway flow limitation is not present in the patient's breath (e.g., at procedure 706 of method 700). In some embodiments, airway flow limitation value subsystem 112 is configured to turn a bit "OFF" (bit is "0"), when it is determined that the airway flow limitation index is less than the airway flow limitation threshold value.

In some embodiments, airway flow limitation value subsystem 112 is configured to determine if the oldest sample/breath in the history buffer represents an airway flow limited breath.

In some embodiments, each time the measured/determined airway flow limitation index is greater than or equal to the airway flow limitation threshold value, a counter is incremented and each time the measured/determined airway flow limitation index is less than the airway flow limitation threshold value, a counter is decremented. System 102 is configured to maintain a history of the last certain number of breaths so that each breath represents a percentage of the history.

In some embodiments, at procedure 708 of method 700, airway flow limitation value subsystem 112 is configured to count the number of history buffer entries indicating the patient is experiencing airway flow limitation. For example, the airway flow limitation value subsystem 112 is configured to count the bits that are turned "ON" or "1" in the predetermined number of desired samples/breaths in the history buffer.

In some embodiments, at procedure 710 of method 700, airway flow limitation value subsystem 112 is configured to compare the number of history buffer entries indicating the patient is experiencing airway flow limitation with a predetermined number of airway flow limited breaths. In some embodiments, the predetermined number of airway flow limited breaths is 10.

If the number of history buffer entries indicating the patient is experiencing airway flow limitation is less than the predetermined number of airway flow limited breaths, airway flow limitation value subsystem 112 is configured to display the airway flow limitation value as zero at procedure 712 of method 700. If the number of history buffer entries indicating the patient is experiencing airway flow limitation is greater than the predetermined number of airway flow limited breaths, airway flow limitation value subsystem 112 is configured to determine the airway flow limitation value at procedure 714 of method 700. For example, the airway flow limitation value, AFLV is determined using Equations (3) and (4) below.

$$AFLV'=(\text{number of airway flow limited breaths}*100)/(\text{number of sample breaths in the history buffer}) \quad (3)$$

$$AFLV=(AFLV'-\text{Ideal percentage})*2 \quad (4)$$

In some embodiments, at procedure 716 of method 700, airway flow limitation value subsystem 112 is configured to display the determined or calculated airway flow limitation value, AFLV to a clinician or a physician. In some embodiments, at procedure 716 of method 700, notification subsystem 116 is configured to display the determined or calculated airway flow limitation value, AFLV to a clinician or a physician.

In some embodiments, at procedure 718 of method 700, airway flow limitation value subsystem 112 is configured to use the determined or calculated airway flow limitation value, AFLV to automatically titrate a patient's pressure therapy that is being delivered by a ventilator device, for instance. In some embodiments, at procedure 718 of method 700, pressure control subsystem 126 is configured to use the determined or calculated airway flow limitation value, AFLV to automatically titrate a patient's pressure therapy that is being delivered by a ventilator device, for instance.

In some embodiments, the determined or calculated airway flow limitation value, AFLV can subsequently be used to guide a physician or a clinician to manually or automatically adjust a patient's pressure therapy that is being delivered by a ventilator device, for instance. In one embodiment, the positive expiratory pressure (PEP) can then be increased until the percentage of flow limited breaths is at its nadir.

In some embodiments, because 'ideal' operation from a clinical perspective is for the feature to oscillate around the airway flow limitation threshold value, the 'ideal' percentage may be 50%. In some embodiments, airway flow limitation value subsystem 112 is configured to display the determined airway flow limitation value (percentage or number) such that a) if the airway flow limited breaths (that are greater than the airway flow limitation threshold value) are between 0 to 50%, the determined airway flow limitation value is displayed as 0%; and b) if the airway flow limited breaths (that are greater than the airway flow limitation threshold value) are between 50 to 100%, the airway flow limitation value, AFLV is determined using Equations (5) and (6) below.

$$AFLV'=(\text{number of airway flow limited breaths}*100)/(20) \quad (5)$$

$$AFLV=(AFLV'-50)*2 \quad (6)$$

For example, in one scenario, the ideal percentage value is 50% (i.e., the predetermined number of breaths is 10) and the number of samples in the history buffer is 20. For example, the number of airway flow limited breaths obtained at procedure 708 of method 700 is 11. As the number of history buffer entries indicating the patient is experiencing airway flow limitation (i.e., 11) is greater than the predetermined number of breaths (i.e., 10), airway flow limitation value subsystem 112 determines the airway flow limitation value at procedure 714 of method 700 as follows:

$$AFLV'=(11*100)/(20)=55$$

$$AFLV=(55-50)*2=10\%$$

In some embodiments, at procedure 716 of method 700, notification subsystem 116 is configured to display the determined or calculated airway flow limitation value, AFLV as 10% to a clinician or a physician. In some embodiments, at procedure 718 of method 700, pressure control subsystem 126 is configured to use the determined or calculated airway flow limitation value, AFLV of 10% to automatically titrate a patient's pressure therapy that is being delivered by a ventilator device, for instance. In some embodiments, the determined or calculated airway flow limitation value, AFLV of 10% can subsequently be used to guide a physician or a clinician to manually or automatically adjust a patient's pressure therapy that is being delivered by a ventilator device, for instance.

In some embodiments, the ideal percentage value is 25%. In such an embodiment, the predetermined number of breaths is 5 (e.g., when the history buffer is limited to 20 samples). In some embodiments, the ideal percentage value is 75%. In such an embodiment, the predetermined number of breaths is 15 (e.g., when the history buffer is limited to 20 samples). In some embodiments, the ideal percentage value may range between 25% and 75%. In such an embodiment, the predetermined number of breaths range between 5 and 15 (e.g., when the history buffer is limited to 20 samples). As noted above, the number of sample breaths in the history buffer may vary.

In some embodiments, notification subsystem 116 may provide a notification regarding the determined airway flow limitation value to one or more other components of system 100. As an example, one or more health monitoring devices 106a ... 106n having one or more sensors 108a ... 108n may obtain health information associated with the patient (e.g., measurements of the airway flow pressure of the patient, measurements of airway flow rate of the patient, measurements of the airway volume of the patient or other health information) and provide the health information to health information subsystem 114. After the health information is processed to determine an airway flow limitation value for the patient, notification subsystem 116 may provide a notification regarding the airway flow limitation value to at least one of a physician or other staff (e.g., a nurse, technician, etc.) who are currently providing primary care via the telehealth services to the patient, and the patient's caretaker, the patient's family member, etc. As one example, notification subsystem 116 may provide a notification regarding the airway flow limitation value via one or more output devices of the health monitoring device) via one or more wired or wireless connections. As another example, notification subsystem 116 may provide a notification regarding the airway flow limitation value to one or more user devices, such as a desktop computer, a notebook computer, a tablet, a smartphone.

In some embodiments, notification subsystem 116 is configured to display or otherwise inform a clinician of a patient's pulmonary status based on flow limitation indices. In some embodiments, the determined airflow limitation value is intended to guide a physician's treatment plan or prescription whenever a pressure therapy is applied to a person's airway. It is generally understood that the percentage of airflow limited breaths and the effectiveness of the pressure therapy/treatment are related. For example, the higher the percentage of airflow limited breaths, the greater the ineffectiveness of the pressure therapy/treatment. If the percent of flow limited breaths is at or near 0%, the pressure therapy/treatment is optimally effective. Whereas, if the percentage of flow limited breaths is closer to 100%, the pressure therapy/treatment is ineffective or minimally effective. Furthermore, it has been demonstrated and widely accepted that the number of breaths that have flow limitation (e.g., expiratory) can be reduced by the application of positive pressure (e.g., during the expiratory phase) of a person's breath cycle. The positive expiratory pressure (PEP) can then be increased until the percentage of flow limited breaths is at its nadir.

Thus, knowledge of the determined airflow limitation value can subsequently be used to guide a physician who chooses to titrate a patient's pressure therapy that is being delivered by a ventilator device, for instance. In some embodiments, the determined airflow limitation value informs the physicians in real time of the effectiveness of a ventilator's pressure setting that has been selected (either manually or automatically) to treat a patient's airway flow limitation, for example, in the positive expiratory pressure setting. In addition, a quantifiable index allows for individualized patient treatment, instead of choosing a therapy that is a "one size fits all" option.

Figure 3:
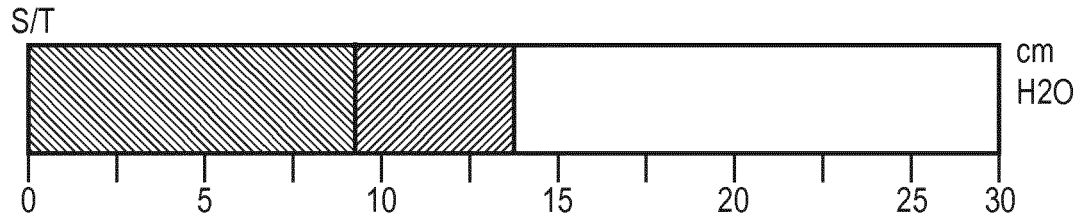
FIG. 3 is an exemplary numerical representation of the determined airway flow limitation value for the patient in accordance an embodiment of the present patent application.
Figure 4:
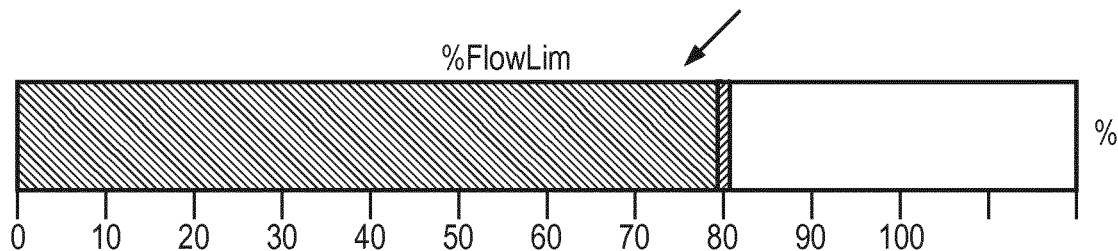
FIG. 4 is an exemplary graphical representation of the determined airway flow limitation value for the patient in accordance an embodiment of the present patent application.

In some embodiments, notification subsystem 116 is configured to display or otherwise inform a clinician of a patient's pulmonary status in a number of ways or formats. For example, FIG. 3 shows an exemplary numerical representation of the determined airway flow limitation value, while FIG. 4 is an exemplary graphical representation of the determined airway flow limitation value in accordance an embodiment of the present patent application. Such a display of the determined airway flow limitation value for the patient allows the clinician to easily evaluate the efficacy of the positive expiratory pressure (PEP) treatment or therapy. In some embodiments, airway flow limitation values are visually provided on a telehealth clinical dashboard or display.

The determined airway flow limitation value for the patient is displayed as a numerical or a percentage value as shown in FIG. 3. For example, determined airway flow limitation value for the patient is displayed as 70%. The determined airway flow limitation value for the patient may be displayed as a graphical bar such as shown in FIG. 4. For example, determined airway flow limitation value for the patient is displayed on the graphical bar as 80%. The graphical bar in FIG. 4, for example, has a range of 0%-100% in increments of 10% for the graphical readout.

A use case scenario for determining an airway flow limitation value in a patient, in accordance with one or more embodiments is described below. As an example, in one scenario, the health information (airway flow information, airway pressure information, etc.) is provided as input to system 100, and the output of system 100 (e.g., an airway flow limitation value) may be provided to the patient, the patient's general practitioner, the patient's medical specialist, or other individual. As an example, after some time, system 100 may flag an alert as a result of the determined airway flow limitation value. Based on this alert, the patient's physician (e.g., general practitioner, medical specialist, etc.) may recommend an adjustment of a patient's pressure therapy that is being delivered by a ventilator device, for instance.

In some embodiments, system 100 may be useful in personal emergency response systems in which a call center agent/personnel needs to decide on an intervention for a subscriber or patient on the basis of the airway flow limitation value. In some embodiments, system 100 may be used in hospital to home programs; clinical programs in ambulatory care, and/or readmission prevention programs. In some embodiments, system 100 may also be used in home monitoring programs; personal emergency response systems, etc.

In some embodiments, the various computers and subsystems illustrated in FIG. 1 may comprise one or more computing devices that are programmed to perform the functions described herein. The computing devices may include one or more electronic storages (e.g., airway flow limitation value database 132, health information database 134, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112, 114, 116, and 126 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112, 114, 116, and 126 described herein is for illustrative purposes, and is not intended to be limiting, as any of subsystems 112, 114, 116, and 126 may provide more or less functionality than is described. For example, one or more of subsystems 112, 114, 116, and 126 may be eliminated, and some or all of its functionality may be provided by other ones of subsystems 112, 114, 116, and 126. As another example, additional subsystems may be programmed to perform some or all of the functionality attributed herein to one of subsystems 112, 114, 116, and 126.

Figure 6:
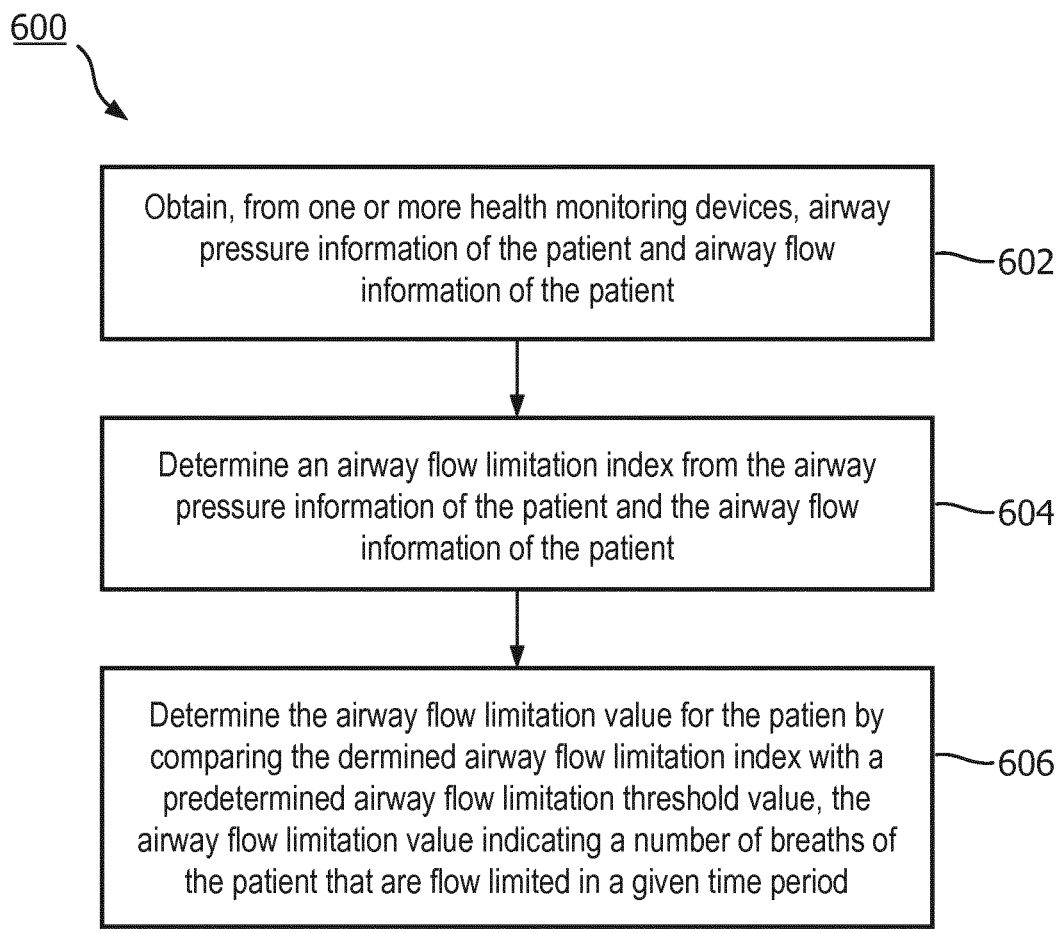
FIG. 6 is a flow chart for determining an airflow limitation value in a patient in accordance an embodiment of the present patent application.

FIG. 6 is a flow chart for determining an airflow limitation value in the patient in accordance an embodiment of the present patent application. Referring to FIG. 6, a method 600 for determining an airway flow limitation value in a patient is provided. Method 600 is implemented by computer system 102 that comprises one or more physical processors executing computer program instructions which, when executed, perform method 600. Method 600 comprises: obtaining, from one or more health monitoring devices 106 (106a . . . 106n), airway pressure information of the patient and airway flow information of the patient at procedure 602; determining, by the computer system, an airway flow limitation index from the airway pressure information of the patient and the airway flow information of the patient at procedure 604; and determining, by the computer system, the airway flow limitation value for the patient by comparing the determined airway flow limitation index with an airway flow limitation threshold value at procedure 606. The airway flow limitation value indicates a number of breaths of the patient that are flow limited in a given time period.

Thus, the present patent application provides a method for computing or determining a patient's airway flow limitation value and for conveying this airway flow limitation value. The airway flow limitation value is based on the percentage or number of valid breaths within a given number of total breaths (or period of time) that are above the airway flow limitation threshold value that is based on the airway flow limitation index.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system for determining an airway flow limitation value in a patient, the system comprising:
   a computer system that comprises one or more first physical processors programmed with first computer program instructions which, when executed cause the computer system to:
      obtain, from one or mom health monitoring devices, airway pressure information of the patient and airway flow information of the patient;
      determine an airway flow limitation index from the airway pressure information of the patient and the airway flow information of the patient, wherein the airway flow limitation index comprises a measurement of a degree of flow limitation of the patient's airways;
      determine the airway flow limitation value for the patient based on the airway flow limitation index and an airway flow limitation threshold value, wherein the airway flow limitation value indicates a number of breaths of the patient that are flow limited during a given time period, and wherein the airway flow limitation threshold value is greater than zero;
      determine whether the number of breaths that are flow limited during the given time period is less than a predetermined number of airway flow limited breaths;
      cause a first airway flow limitation value to be displayed as the airway flow limitation value responsive to determining that the number of breaths is less than the predetermined number of airway flow limited breaths, wherein the first airway flow limitation value is a constant value;
      cause a second airway flow limitation value to be displayed as the airway flow limitation value responsive to determining that the number of breaths is greater than or equal to the predetermined number of airway flow limited breaths, wherein the second airway flow limitation value is computed based on the number of breaths and the predetermined number of airway flow limited breaths; and
      automatically adjust, via a pressure control subsystem that is part of the computer system, a pressure of a pressure therapy applied to the patient's airway based on the first airway flow limitation value or the second airway flow limitation value,
   wherein:
   the first airway flow limitation value and the second airway flow limitation value are represented as percentages indicating a percentage of breaths of the patient during the given time period that are flow limited,
   the constant value is 0%; and
   the second airway flow limitation value is computed by:
      determining a percentage of flow limited breaths of the patient during the given time period, and
      determining a difference between the percentage of flow limited breaths of the patient during the given time period and ideal percentage of flow limited breaths during the given time period, wherein the second airway flow limitation value equals twice the difference, and the ideal percentage of flow limited breaths is predetermined based on the predetermined number of airway flow limited breaths.

2. The system of claim 1, wherein each of the one or more health monitoring devices comprises:
one or more sensors programmed to obtain the airway pressure information of the patient and the airway flow information of the patient, and
one or more second physical processors programmed with second computer program instructions which, when executed, cause the one or more health monitoring devices to:
obtain, based on the one or more sensors, the airway pressure information of the patient and the airway flow information of the patient; and
provide the airway pressure information of the patient and the airway flow information of the patient to the computer system for determining the airway flow limitation index.

3. The system of claim 1, wherein the airway flow limitation threshold value is determined based on previously obtained airway pressure information from a plurality of patients and airway flow information from the plurality of patients, the computer system is further caused to:
continuously obtain subsequent airway pressure information of the plurality of patients and subsequent airway flow information of the plurality of patients; and
continuously modify the airway flow limitation threshold value based on the subsequent airway pressure information and the subsequent airway flow information.

4. A method for determining an airway flow limitation value in a patient, the method being implemented by a computer system that comprises one or more physical processors executing computer program instructions which, when executed, perform the method, the method comprising:
obtaining, from one or more health monitoring devices, airway pressure information of the patient and airway flow information of the patient;
determining, by the computer system, an airway flow limitation index from the airway pressure information of the patient and the airway flow information of the patient, wherein the airway flow limitation index comprises a measurement of a degree of flow limitation of the patient's airways;
determining, by the computer system, the airway flow limitation value for the patient based on the airway flow limitation index and an airway flow limitation threshold value, wherein the airway flow limitation value indicates a number of breaths of the patient that are flow limited during a given time period, and wherein the airway flow limitation threshold value is greater than zero;
determining, by the computer system, whether the number of breaths that are flow limited during the given time period is less than a predetermined number of airway flow limited breaths;
causing, by the computer system, a first airway flow limitation value to be displayed as the airway flow limitation value responsive to determining that the number of breaths is less than the predetermined number of airway flow limited breaths, wherein the first airway flow limitation value is a constant value;
causing a second airway flow limitation value to be displayed as the airway flow limitation value responsive to determining that the number of breaths is greater than or equal to the predetermined number of airway flow limited breaths, wherein the second airway flow limitation value is computed based on the number of breaths of the patient that are flow limited and the predetermined number of airway flow limited breaths; and
automatically adjusting by a pressure control subsystem that is part of the computer system, a pressure of a pressure therapy applied to the patient's airway based on the first airway flow limitation value or the second airway flow limitation value,
wherein:
the first airway flow limitation value and the second airway flow limitation value are represented as percentages indicating a percentage of breaths of the patient during the given time period that are flow limited;
the constant value is 0%; and
the second airway flow limitation value is computed by:
determining a percentage of flow limited breaths of the patient during the given time period, and
determining a difference between the percentage of flow limited breaths of the patient during the given time period and an ideal percentage of flow limited breaths during the given time period, wherein the second airway flow limitation value equals twice the difference, and the ideal percentage of flow limited breaths is predetermined based on the predetermined number of airway flow limited breaths.

5. The method of claim 4, wherein is determined based on previously obtained airway pressure information from a plurality of patients and airway flow information from the plurality of patients, the method further comprises:
continuously obtaining, by the computer system, subsequent airway pressure information of the plurality of patients and subsequent airway flow information of the plurality of patients; and
continuously modifying, by the computer system, the airway flow limitation threshold value based on the subsequent airway pressure information and the subsequent airway flow information.

6. A system for determining an airway flow limitation value in a patient, the system comprising:
a means for executing machine-readable instructions with at least one processor, the machine-readable instructions, when executed, effectuating operations comprising:
obtaining, from one or more health monitoring devices, airway pressure information of the patient and airway flow information of the patient;
determining an airway flow limitation index from the airway pressure information of the patient and the airway flow information of the patient, wherein the airway flow limitation index comprises a measurement of a degree of flow limitation of the patient's airways;
determining the airway flow limitation value for the patient based on the airway flow limitation index and an airway flow limitation threshold value, wherein the airway flow limitation value indicates a number of breaths of the patient that are flow limited during a given time period, and wherein the airway flow limitation threshold value is greater than zero;
determining whether the number of breaths that are flow limited during the given time period is less than a predetermined number of airway flow limited breaths;

causing a first airway flow limitation value to be displayed as the airway flow limitation value responsive to determining that the number of breaths is less than the predetermined number of airway flow limited breaths, wherein the first airway flow limitation value is a constant value; and causing a second airway flow limitation value to be displayed as the airway flow limitation value responsive to determining that the number of breaths is greater than or equal to the predetermined number of airway flow limited breaths, wherein the second airway flow limitation value is computed based on the number of breaths of the patient that are flow limited and the predetermined number of airway flow limited breaths; and automatically adjusting, using the means for executing and a pressure control subsystem, a pressure of a pressure therapy applied to the patient's airway based on the first airway flow limitation value or the second airway flow limitation value, wherein:

the first airway flow limitation value and the second airway flow limitation value are represented as percentages indicating a percentage of breaths of the patient during the given time period that are flow limited, the constant value is 0%; and the second airway flow limitation value is computed by,
determining a percentage of flow limited breaths of the patient during the given time period, and
determining a difference between the percentage of flow limited breaths of the patient during the given time period and an ideal percentage of flow limited breaths during the given time period, wherein the second airway flow limitation value equals twice the difference, and the ideal percentage of flow limited breaths is predetermined based on the predetermined number of airway flow limited breaths.

7. The system of claim 6, wherein the airway flow limitation threshold value is determined based on previously obtained airway pressure information from a plurality of patients and airway flow information from the plurality of patients, the operations further comprise:

continuously obtaining subsequent airway pressure information of the plurality of patients and subsequent airway flow information of the plurality of patients; and
continuously modifying the airway flow limitation threshold value based on the subsequent airway pressure information and airway flow information.

8. The system of claim 1, wherein:

the airway pressure information of the patient and the airway flow information of the patient are used to determine a respiratory system reactance during inspiration and a respiratory system reactance during expiration; and the airway flow limitation index is determined based on the respiratory system reactance during inspiration and the respiratory system reactance during expiration.

9. The system of claim 1, wherein the computer system is further caused to:

cause a bit in a bitmask to be stored as a first value in response to determining that the airway flow limitation index is greater than or equal to the airway flow limitation threshold value; and cause the bit in the bitmask to be stored as a second value in response to determining that the airway flow limitation index is less than the airway flow limitation threshold value, wherein the airway flow limitation value is further determined based on:

a number of bits in the bitmask having the first value and a predetermined number of airway flow limited breaths, wherein the number of bits in the bitmask having the first value corresponds to the number of breaths of the patient that are flow limited during the given time period.

10. The system of claim 9, wherein determining whether the number of breaths is less than the predetermined number of airway flow limited breaths is based on the number of bits in the bitmask having the first value.

11. The system of claim 1, wherein the pressure of the pressure therapy being adjusted comprises:

determining a current airway flow limitation value, wherein a current pressure of the pressure therapy is based on the current airway flow limitation value;

causing the pressure of the pressure therapy to be increased from the current pressure to an increased pressure in response to determining that the airway flow limitation value is greater than the current airway flow limitation value; and causing the pressure of the pressure therapy to be decreased from the current pressure to a decreased pressure in response to determining that the airway flow limitation value is less than the current airway flow limitation value.

* * * * *